United States Patent [19]

Kass

[11] Patent Number: 4,810,487
[45] Date of Patent: Mar. 7, 1989

[54] METHOD OF IDENTIFYING POLYMETHINE STAINED LYMPHOCYTE SUBPOPULATIONS AND COMPOSITIONS THEREOF

[75] Inventor: Lawrence Kass, Hinckley, Ohio
[73] Assignee: Cytocolor, Inc., Hinckley, Ohio
[21] Appl. No.: 812,918
[22] Filed: Jan. 2, 1986
[51] Int. Cl.⁴ .......................... G01N 1/00; C12Q 1/02
[52] U.S. Cl. ......................................... 424/3; 424/7.1; 435/29; 435/34; 436/116; 436/176; 436/805; 436/811; 514/415; 548/490
[58] Field of Search ............ 424/3, 7, 1; 435/29, 435/34; 436/166, 176, 805, 811; 514/415; 548/490

[56] References Cited
U.S. PATENT DOCUMENTS

| | | | |
|---|---|---|---|
| 4,400,370 | 8/1983 | Kass | 424/7.1 X |
| 4,500,509 | 2/1985 | Kass | 424/7.1 X |
| 4,513,142 | 4/1985 | Raue et al. | 548/490 X |
| 4,581,223 | 4/1986 | Kass | 424/7.1 X |
| 4,615,878 | 10/1986 | Kass | 424/7.1 X |
| 4,714,606 | 12/1987 | Kass | 435/29 X |

Primary Examiner—Esther M. Kepplinger
Assistant Examiner—Richard Wagner
Attorney, Agent, or Firm—Pearne, Gordon, McCoy & Granger

[57] ABSTRACT

This invention is directed to the use of specific polymethine dyes for staining fixed biopsy specimens of hematopoietic origin consisting of blood, bone marrow and lymph node cells for purposes of identifying and enumerating the stained cells when viewed under dark field illumination. The polymethine dyes, e.g. Astrazon Red Violet FRR, stain the lymphocyte subpopulations distinct colors capable of being viewed under dark field illumination for purposes of distinguishing one stained cell from another. This method of staining and the compositions thereof represents an advance in the art of lymphocyte subpopulation identification which was achieved heretofore primarily by using monoclonal antibody techniques.

30 Claims, 4 Drawing Sheets

T-HELPER CELLS
(BRIGHT RED)

T-SUPPRESSOR CELLS
(YELLOW-ORANGE)

B-CELLS
(YELLOW)

NATURAL KILLER (NK) CELLS
(GREEN)

FIG. 1

FIG. 2

WAVELENGTH IN nm
(ASTRAZON VIOLET F$_3$RL)
(BV21)

FIG. 3

T-HELPER CELLS
(BRIGHT RED)

T-SUPPRESSOR CELLS
(YELLOW-ORANGE)

B-CELLS
(YELLOW)

NATURAL KILLER (NK) CELLS
(GREEN)

FIG. 4

NEUTROPHIL

MONOCYTE

BASOPHIL

EOSINOPHILS

T-HELPER CELLS

T-SUPPRESSOR CELLS

B-CELLS

NATURAL KILLER (NK) CELLS

METHOD OF IDENTIFYING POLYMETHINE STAINED LYMPHOCYTE SUBPOPULATIONS AND COMPOSITIONS THEREOF

BACKGROUND OF THE INVENTION

This invention is directed to the use of a single, substantially pure, polymethine dye for the cytological preparation of a fixed biopsy specimen of hematopoietic origin. More specifically, this invention relates to the use of a single polymethine dye for differentiating, identifying and enumerating cells among a plurality of cells of hematopoietic origins selected from the group consisting of blood cells, bone marrow cells and lymph node cells. The polymethine dyes of this invention can be used to stain a plurality of lymphocytes of hematopoietic origin by treating a fixed biopsy specimen with a solution of the polymethine dye and subsequently identifying and enumerating the stained cells under dark field illumination. The polymethine dyes particularly useful for purposes of this invention are available as Astrazon Violet $F_3$ RL (BV 21) and Astrazon Red Violet FRR. The stained lymphocyte subpopulations prepared in accordance with this invention have excellent color stability, are remarkably clear with respect to cellular detail and have brilliant cell structure.

In general, there are various methods for counting and classifying leukocytes. For example, the cytotechnician microscopically views a biopsy specimen prepared on an ordinary microscope slide that has been stained with one of the Romanowsky stains. The cytotechnician examines the stained leukocytes and classifies them according to cell type. This method, however, is time consuming and has the disadvantage of not being reliable with respect to counting and classifying the less abundant cells such as the monocytes, eosinophils, basophils, etc. In a typical automated system, a biopsy specimen is stained in the usual manner with a Romanowsky stain and then scanned mechanically under a microscope provided with an electronic image tube. When the leukocyte comes in view of the image tube, the slide is stopped. An image analyzing computer connected to the image tube classifies the leukocyte according to its cell profile and cytoplasm color. Here also, the system suffers from the disadvantage of being too time consuming and costly.

In comparison, the use of the polymethine dyes of this invention is an improvement over the Romanowsky stains even though mixtures of dyes are still the basis for morphological hematology and are being used for the identification of cells. The Romanowsky-type stains are commonly known to contain Methylene Blue and eosin. The mixture of dyes produces the Romanowsky effect defined as a condition wherein the coloration of the cell components results from the combined action of the mixture of dyes, and cannot be produced by either dye acting alone. The state of the art as presently developed, fails to teach the use of a single, substantially pure, commercially available dye capable of panoptically and metachromatically staining a fixed biopsy specimen. The polymethine dyes of this invention, however, are capable of staining cells of hematopoietic origin comprising blood cells, bone marrow cells or lymph node cells which permits the differentiation, enumeration and identification of the individual cells, i.e. the subpopulations of lymphocytes including the abnormal or malignant cells.

In recent years, the identification of lymphocytes and their various subpopulations has become more important and more interesting to biomedical researchers especially for diagnostic purposes. More particularly, the various subpopulations of lymphocytes have been better defined and described and their functions in the immune system have become more clearly delineated. More specifically, the important subpopulations include the B-cells, T-helper cells, T-suppressor cells, and Natural Killer (NK) cells. The B-cells are believed to be bursa derived and are involved in the synthesis of circulating immunoglobulins. According to recent evidence, the T-helper and T-suppressor cells are involved in the modulation of the immune response and in the regulation of erythropoiesis. More important, the Natural Killer cells represent the body's first line of defense against malignancy, since these cells are directly cytotoxic to any foreign cells, and do not require the mediation of complement to effect their lysis.

Within the past several years, however, the function and complexity of the T-helper and T-suppressor cell populations have received an increasing amount of attention. Currently, it is believed that the HTLV-I virus is the specific etiologic agent for adult T-cell leukemia. This virus specifically attacks the T-helper cell by entering the genetic material and "immortalizes" the cell, transforming it into a large leukemic lymphoblast with striking convolutions and indentations of the nucleus and containing a large nucleolus. Presumably, the HTLV-I virus particles replicate within the T-helper cell and are shed into the circulation system to infect other T-helper cells.

In contrast to the "immortalization" of the T-helper cell in the HTLV-I virus infestation, the HTLV-III virus infects the T-helper cells specifically and in so doing destroys the cells. It is important to note that the HTLV-III virus is believed to be the specific causative agent of the acquired immune deficiency syndrome (AIDS). In this disorder (AIDS), it was found that the number of T-helper cells is greatly diminished because of the lethal effects of the virus, leading to a reversal of the ratio between the T-helper cell and the T-suppressor cell. Morevoer, information about the antibodies to the HTLV-III virus, and the ratio of the T-helper to the T-suppressor cells is a valuable diagnostic test for determining the presence of HTLV III infection, and also for confirming the diagnosis of AIDS.

Further, the identification and enumeration of the various lymphocyte subpopulations continues to be increasingly important in other disorders of presumed immune origin, such as collagen diseases and the allergic disorders as well as in the investigation of malignancies and the role of the immune system in the defense against malignancies. Studies have also demonstrated that there are abnormalities in the T-cell subset populations in patients with malignancies treated with chemotherapy. Whether or not disturbances in these immune mechanisms and in the mechanisms of immune surveilance contribute to the development of malignancies and to the ultimate development of acute leukemia in patients treated with chemotherapy is a provocative and as of now an unanswered question.

The prior art teaches that the identification of the various lymphocyte subpopulations can be achieved, for the most part, with the use of rosette formations using either untreated sheep red blood cells for T-cells and treated sheep red blooded cells for B-cells. Another more common method is the use of monoclonal antibodies direct against specific surface antigens on the various lymphocytes. Although these antibodies are expensive to use and require a tedious methodology, the monoclonal antibodies are highly specific. However, because of their complexity, particularly with respect to sample preparation, the monoclonal antibodies have not been in widespread use in the smaller hospitals, laboratories, physicians offices, clinics and the like.

Initially, Kass taught that the identification of T-cells and B-cells and in several cases other lymphocyte subpopulations could be accomplished by using a single organic dyestuff; see U.S. Pat. Nos. issued to Dr. L. Kass Nos. 4,400,370 and 4,500, 509 and U.S. patent application Ser. Nos. 129,680 filed Mar. 12, 1980; 604,741 filed Apr. 27, 1984; 604,869 filed Apr. 27, 1984; and 765,348 filed Aug. 13, 1985. The Kass patents disclose that Basic Orange 21 is a supravital stain and therefore must be used on living blood cells in a liquid suspension viewed in the presence of absorbance or fluorescent light. The Basic Blue 41 dye, however, must be used on a fixed biopsy specimen. Here the lymphocyte subpopulations were identified on the basis of the difference in the intensity of staining and the caliber of the nuclear chromatin strands in the nucleus, as well as the presence of metachromatically staining granules in the cytoplasm. By using the Basic Blue 41 stain, the lymphocyte subpopulations could be identified under absorbance light, since the cells do not fluoresce nor do they demonstrate differential coloration when viewed under dark field illumination. However, by using still another stain, i. e. Basic Blue 141, the B-cell and T-cell subpopulations displayed differential staining in a fixed biopsy specimen but the cells did not fluoresce, nor did they exhibit any differential coloration when viewed under a dark field illumination.

Accordingly, it is an object of this invention to provide a single, substantially pure, polymethine dye for staining fixed cells of hematopoietic origin for the identification and enumeration of lymphocyte subpopulations.

It is another object of this invention to provide a single polymethine dye capable of staining lymphocyte subpopulations of hematopoietic origin which can be viewed under dark field illumination for purposes of identification and enumeration.

It is another object of this invention to provide novel stained cells of hematopoietic origin, and more particularly stained lymphocyte subpopulations of hematopoietic origin having individual color characteristics which permit the differentiation, identification and enumeration of said cells.

It is a further object of this invention to provide a method of staining a plurality of cells of hematopoietic origin by reacting a single polymethine dye with a fixed biopsy specimen to obtain a plurality of stained cells having individual color characteristics which permit the differentiation, identification and enumeration of said stained cells under dark field illumination. These and other objects of the invention will become apparent from a further more detailed description of the invention as follows.

SUMMARY

This invention relates to the method of differentiating, identifying and enumerating cells and particularly human cells from each other among a plurality of cells of hematopoietic origin selected from the group consisting of blood cells, bone marrow cells, and lymph node cells. The method comprises fixing a biopsy specimen of hematopoietic origin, i.e. lymphocyte subpopulations in a fixative, e.g. solution of alcohol which may contain effective amounts of an alkaline buffering agent and subsequently staining the fixed biopsy specimen, e.g. fixed blood cells with staining amounts of a single polymethine dye. For purposes of this invention, the only polymethine dyes that can be used to stain the lymphocyte subpopulations include Astrazon Violet F$_3$RL Colour Index No. 48030 (Basic Violet 21), Astrazon Red Violet FRR, and Astraphloxine Violet, Colour Index No. 48025. The plurality of cells of hematopoietic origin including blood cells, lymph node cells, and bone marrow cells may comprise both normal and abnormal cells, i.e. the plurality of cells may contain malignant or abnormal cells. The cells or lymphocyte subpopulations stained with either of the polymethine dyes of this invention have individual color characteristics which enable the cells to be differentiated and enumerated, one from the other, by use of various instruments, e.g. microscope, under a dark field illumination.

The three specific polymethine dyes useful for staining cells in accordance with this invention have the basic formula:

FORMULA I wherein R is a substituent selected from the group consisting of hydrogen, carboxyl methyl ester group, i.e.

and chlorine. The nomenclature for this particular basic dye is p-ethoxyphenyl-p-aminostyryl-1,3,3-trimethyl-3H-indolium chloride. This particular dye is only one of the three species, having the basic structure identified above, which can be used for purposes of this invention. The three species differ, one from the other, by the presence on the benzene ring of the R substituent which is either a hydrogen atom, chlorine atom, or carboxyl methyl ester group, i.e.

The chlorine substituted species is identified as 5-chloro-1,3,3-trimethyl-2-methylene indoline. The carboxyl ester substituted species is identified as 1,3,3-trimethyl-2-methylene-5-indoline carboxylic acid methyl ester.

In accordance with this invention, when an aqueous solution of either one of the three species of dye is applied to or reacted with a fixed biopsy specimen containing blood, bone marrow, or lymph nodes, etc. and then viewed under dark field illumination, the various lymphocyte subpopulations showed a striking intensification of colors that were different for each cell. More specifically, the T-helper cells stained red, the T-suppressor cells stained yellow-orange, the B-cells stained yellow, and the Natural Killer cells stained green. The identification of the T-helper cells, which is very important to the diagnostic studies relating to HTLV-I and HTLV-III infections, was generally facilitated by either of these three species of dye in that the cells illuminated bright red in color.

In addition to Astrazons Red Violet FRR, F3RL and Astraphloxine Violet, many other readily available poly methine dyes were tested as stains for lymphocyte subpopulations under dark field illumination. Some of the dyes that were tested included Basic Blue 62, 69, 145 and 147. Other Colour Index Basic Red dyes tested included 12, 13, 15, 27, 35, 36, 49, 52, 53, and 68. The Colour Index Basic Orange dyes tested included 21, 22, 27, 42, 44, and 46. The Colour Index Basic Yellow dyes tested included 13, 23, 24, 28, 40, 45, 49, 52, 53, and 63. The Colour Index Basic Violet dyes tested included 7, 15, 16, 20, 21, 39, and 40. In addition to the above, many other cationic textile dyes were tested. Of all of the different dyes tests, it was found, however, that only the three species disclosed herein were capable of staining the lymphocyte subpopulations to the degree required for dark field illumination.

Figure 1:
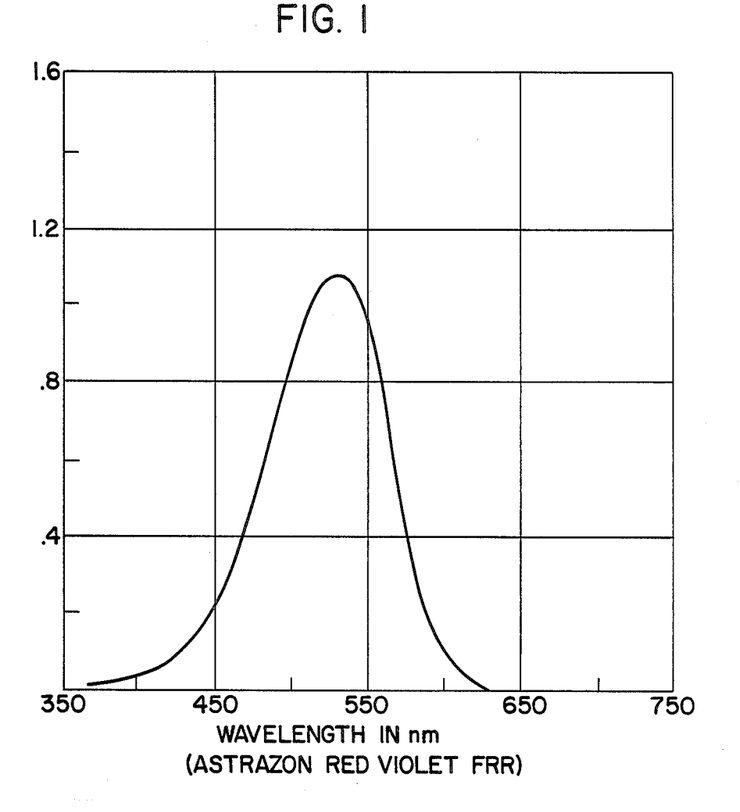
Figure 2:
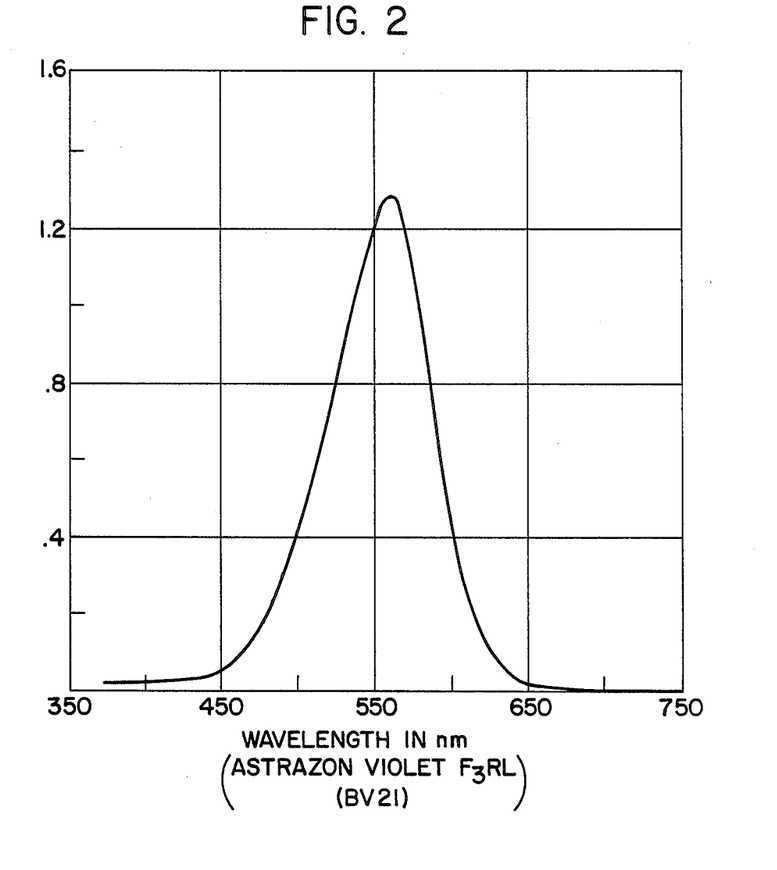

Astraphloxine Violet and Astrazon Violet F3RL are identified in the Colour Index by Numbers 48025 and 48030 (Colour Index 1971 Edition). Astrazon Violet F3RL is also identified as BV21. Of the many dyes identified, however, Astrazon F3RL and FRR were the only polymethine dyes that exhibited similar differential coloration of lymphocyte subpopulations when viewed under dark field illumination. In fact, Astrazon Red Violet FRR was to some degree superior to Astrazon Violet F3RL (Basic Violet 21) in that Astrazon Red Violet FRR produced more intense coloration of the cells. Because of the similarity in the staining reaction, and the ambiguity of the structure of Astrazon Red Violet FRR, samples of this dye, found to be greater than 97% pure, were subjected to structural analysis utilizing carbon-13 off-resonance, carbon-13 NMR spectrum, and proton-H spectrum. Each of these analytical tests resulted in the same chemical formula for Astrazon Red Violet FRR, as shown in Formula I hereof, i.e. p-ethoxyphenyl-p-aminostyryl-1,3,3-trimethyl-3H-indolium chloride. The chemical structure for Astrazon Violet F3RL (Basic Violet 21), is the same as Astrazon Red Violet FRR, except Astrazon Violet F3RL contains a carboxyl methyl ester group, i.e.

substituent at the C5 position of the benzene ring. FIG. 1 shows the spectral curve of Astrazon Red Violet FRR as having a wavelength peak at 535 nm. FIG. 2 shows Astrazon Violet F3RL (Basic Violet 21) as having a wavelength peak at 560 nm.

It was found, however, that when using either Astrazon dyes F3RL or FRR as a supravital stain in the process taught in U.S. Pat. Nos. 4,400,370 and 4,500,509, i.e. Basic Orange 21, neither of the polymethine dyes of this invention produced any staining of the lymphocytes. Moreover, by using absorbance or fluorescent illumination of the cells, stained with either Astrazon Red Violet FRR or Astrazon Violet F3RL, it was found that no consistent differences could be detected among the various cell types found in the blood, bone marrow or lymph nodes. Particularly of interest is the fact that there was no difference in the coloration of lymphocyte subsets under absorbance, and no detection of fluoresence.

More specifically, the three polymethine stains of this invention were used for staining biopsy specimens in accordance with the following procedure. A fixed coverslip or slide preparation of blood, bone marrow, buffy coat, or lymph node was fixed in a FAA fixative. FAA is a fixative which comprises 90 ml. of 95% ethanol, 5 ml. of glacial acetic acid, and 5 ml. of 37% formalin. Depending on the concentration, the coverslips or slides were fixed in the fixative for periods ranging up to about ten minutes or more and then washed with running tap water, e.g. for about a minute. Depending on the concentration of dye, the fixed biopsy specimens were subsequently stained for periods ranging from about 1 to 10 minutes, e.g. approximately five (5) minutes with about a 1% to 3% aqueous solution of Astrazon Red Violet FRR (see Formula I), which was filtered before being used on the specimen. Subsequent to staining, the biopsy specimens were thoroughly washed with gentle agitation for periods of about 15 seconds to about one minute or more in 2-amino-2-hydromethyl 1,3 propane diol, i.e. a commercial buffer solution containing about 0.05 moles of buffering agent per liter with a pH of 7.6. Subsequently, the stained and washed biopsy specimens were air dried and mounted with a conventional resin mounting media on clean glass slides and then viewed under dark filed illumination. The results of treating the biopsy specimens by the process set forth hereinabove is set forth in Table I.

TABLE I

Peripheral blood leukocytes were fixed with the FAA fixative, stained with Astrazon Red Violet FRR and then viewed under dark field illumination in accordance with this invention.

| Cell | Nucleus and Nuclear Membrane | Cytoplasmic Membrane | Cytoplasm |
|---|---|---|---|
| Neutrophils | pale green | pale green | deep red/black granules |
| Monocytes | pale green | pale green | few pale green inclusions |
| Eosinophils | pale green | pale green | bright sky-blue granules |
| Basophils | pale green | pale green | bright yellow granules |
| T-helper cell | bright red/orange | bright red/orange | red/orange |
| T-suppressor cell | bright yellow/orange | bright yellow/orange | yellow/orange |
| B-cell | yellow | yellow | yellow annular appearing inclusions |
| Natural Killer (NK) cell | pale green | pale green | few bright yellow to yellow green inclusions |

It was found that in normal peripheral blood or in buffy coat preparations, the neutrophils stained dark greenish-red, the erythrocytes stained orange-yellow, the granules in the eosinophils stained bright blue, the granules in basophils stained bright yellow, the monocytes demonstrated pale green staining of the nucleus and cytoplasm and the platelets appeared pale green. From examination under dark field illumination, at least four types of lymphocytes were detected. One of the types showed bright red staining of the nucleus and particularly the cytoplasm. The second type showed the yellow to orange staining of the nucleus and the cytoplasm. The third type showed the yellow staining of the nucleus and cytoplasm, and the fourth type showed the bright green staining of the nucleous and cytoplasm with greenish cytoplasmic inclusions.

For further analysis of the T-cell and B-cell subpopulations, and for identification of the specific type of lymphocytes in the peripheral blood, 100 cc of normal peripheral venous blood from three different volunteers was subjected to cell sorting in a commercial cell sorter. Using monoclonal antibodies, the following lymphocyte subpopulations were obtained: SIg for B-cells, OKT-4 for the T-helper cells, OKT 8 for T-suppressor cells, and Leu 11b for Natural Killer (NK) cells. The lymphocyte subpopulations, which were 98–99% pure with respect to homogeneity, were deposited on clean glass sides by cytocentrifugation, air dried, stained with Astrazon Red Violet FRR, as described hereinabove, and then viewed under dark field illumination. The following results were obtained: The B-cells stained bright yellow, particularly the cytoplasm. The T-helper cells stained bright red, especially the cytoplasm. The T-suppressor cells stained yellow-orange, particularly in the cytoplasm. The Natural Killer cells stained bright green. The intense bright red color of the T-helper cells and the striking difference in coloration between the T-helper cells and the T-suppressor cells, under dark field illumination, permitted a sharp distinction between the two cell types based solely on color.

Using fluorescent light, none of the lymphocyte subsets stained with Astrazon Red Violet FRR showed fluorescence. By using absorbance, some difference in the intensity of staining could be observed when comparing different types of lymphocytes, but the coloration (a violet or lavender color) was the same and no differential coloration could be detected using white light. Moreover, the dye (Astrazon Red Violet FRR) per se does not exhibit coloration under dark field illumination. This suggests that only when the Astrazon Red Violet dye is bound or reacted with the cellular structure of the cell does the coloration become obvious under dark field illumination.

Where bone marrow cells were stained with Astrazon Red Violet FRR, precursor cells of the more mature cells found in the blood could be identified on the basis of similar staining patterns, although to a lesser degree than in the more mature cells. Particularly, the normoblasts (nucleated red blood cells) often confused with lymphocytes because of their similar size and shape, stained very differently from the lymphocytes when Astrazon Red Violet FRR was used as the stain. The normoblasts displayed bright yellow nuclei and dull magenta cytoplasm in contrast to the bright red cytoplasmic staining found in lymphocytes. This was true even after removal of RNA from the cells with ribonuclease and subsequent staining with Astrazon Red Violet FRR. The brilliant colors seen in the lymphocytes under dark field illumination were undiminished compared to the untreated cells. This finding suggests that the staining reaction was not due simply to staining of RNA by the dye.

Accordingly, it is evident from the data presented herein, that the use of either of the three species of polymethine dyes for staining biopsy specimens in accordance with this invention, has definite advantages over the use of the monoclonal antibody technique for lymphocyte subpopulation identification. More specifically, it was found that in accordance with this invention, the biopsy specimen requires only a brief fixation prior to the staining process and that only a simple preparation is necessary in comparison to the complex methology required of most monoclonal techniques, i.e. the requirements of centrifugation, incubation, washing, etc. Moreover, the process of using the polymethine dyes of this invention is an improvement over the other techniques in that it is rapid in terms of the amount of time needed for the staining reaction. The present process is relatively inexpensive and the stained specimens can be differentiated and identified with ordinary white light laboratory equipment, e.g. microscopes equipped with a dark field condenser. It was found that the color distinction of the stained biopsy specimens, under the dark field illumination, was unusually intense and reproduceable making it very easy to distinguish the lymphocyte subpopulations on the basis of the differences in color alone. Moreover, the polymethine stains as taught herein are permanent and were found not to fade on storage, i.e. storage of sides were permanent over appreciable periods of time.

The fixatives which may be utilized for fixing the biopsy specimens in accordance with this invention, are generally well known and include the alcohols such as methanol or ethanol, formaldehyde and the like. In general, fixing the biopsy specimens or tissue is accomplished by using a neutral buffered solution of formalin or absolute alcohol such as methanol. A buffered solution of formalin is a general purpose fixative. Fixatives useful for purposes of this invention, e.g. staining of biopsy specimens, may be found in the text by S. W. Thompson and R. D. Hunt entitled *Selected Histochemical Histopathological Methods,* published by Charles C. Thomas, Springfield, Illinois.

In general, the biopsy specimens of hematopoietic origin are initially exposed to a fixative such as alcohol, e.g. methanol, at ambient temperatures. After washing off the fixative with either water and/or alcohol, the fixed cells, e.g. human blood cells, are subsequently stained with staining amounts of an aqueous solution containing up to 2% and preferably up to 1% by weight of one of the polymethine dyes. The aqueous solution of Astrazon Violet FRR, for example, may be solubilized in water alone or in water containing one or more buffering agents. Another method of fixing and staining the biopsy specimens includes initially fixing the cells in a methanolic solution containing the dye and then further staining the fixed cells in the presence of effective amounts of an alkaline buffering agent in an aqueous solution containing additional amounts of dye. In other words, the cells are fixed and stained in the alcohol containing the dye but the color characteristics are further developed by the addition of a buffered, aqueous solution of the dye directly to the methanolic solution. In another method, the biopsy specimens are fixed in a methanolic solution containing the dye and then further developed by the addition of an alkaline buffering solution to the methanolic solution.

More specifically, the process of staining the biopsy specimens in accordance with this invention may include a number of variations without departing from the spirit of the invention. First, a methanolic solution of the dye is added to the biopsy specimen for periods of up to about five minutes, then an aqueous alkaline buffer is added to the methanolic solution containing the dye. After about three minutes, the slides were washed in aqueous alkaline buffer, dried and mounted. Second, a methanolic solution of the dye is applied to the biopsy specimen for periods of up to three minutes and then an aqueous alkaline buffered solution of the dye is added directly to the methanolic solution containing the dye. After about five minutes the stained cells are washed with an alkaline buffer, dried and mounted. Third, biopsy specimens were fixed in absolute methanol for about up to three minutes and the methanol was washed off with distilled water. Subsequently, the fixed cells were stained with an aqueous alkaline buffered solution containing the dye for periods of up to five minutes and washed with an alkaline aqueous solution of buffer, dried and mounted. The method of fixing the biopsy specimens is not critical, but as a matter of convenience and to get the utmost in color differentiation the above outlines the preferred process for fixing the biopsy specimens prior to staining or simultaneously with staining by using the fixative alone or by combining the dye with the fixative which may contain a buffering agent to adjust the pH.

The reagents useful for adjusting the pH of the fixative and/or aqueous solution of the dye, include a variety of acids and bases such as the salts of weak acids. Specifically, the buffer includes sodium hydroxide, potassium hydroxide, metal phosphates, acetates, carbonates, borates, acetic acid, ammonia, etc. The buffering agents useful for purposes of this invention can be found in the text by Williams & Chase entitled *Methods in Immunology and Immunochemistry*, Vol. II, Academic Press, New York (1968).

The following are specific illustrations of using Astrazon Violet FRR, a polymethine dye identified herein, for staining fixed biopsy specimens.

EXAMPLE I

A 28 year old white male was admitted to the hospital with cough and lymphadenopathy. On physical examination, the male appeared chronically ill, and enlarged lymph nodes were found in the neck. On laboratory evaluation, the male was found to have anemia. Analysis of the T and B-cell subpopulations showed a reversal of the normal ratio when analyzed by the monoclonal antibody technique. Further analysis of the lymphocyte subpopulations with Astrazon Red Violet FRR, as identified herein and when viewed under dark field illumination, clearly showed a substantial decrease in the number of red colored lymphocytes (T-helper cells). This finding substantiates the results obtained with the monoclonal antibodies test. The final diagnosis of the man's illness was Acquired Immune Deficiency Syndrome (AIDS).

EXAMPLE II

A 49 year old woman was admitted to the clinic because of fatigue. On physical examination, she was found to have enlarged lymph nodes in the neck and an enlarged spleen. Laboratory values revealed a white blood cell count of 200,000 per $mm^3$ and on differential blood cell count, 98% of the lymphocytes were seen. A bone marrow examination revealed a replacement of the marrow by lymphocytes. On monoclonal antibody evaluation of the peripheral blood lymphocytes, almost all of the lymphocytes were of the B-cell type. By using Astrazon Red Violet FRR (polymethine dye as defined herein) it was found that nearly all of the lymphocytes stained yellow. The woman was diagnosed as having chronic lymphocytic leukemia of the B-cell type.

The identification and enumeration of the subpopulations of lymphocytes including the T-cells and B-cells, which are the major lymphocyte populations in man, are basic to the understanding of the immune system and the various diseases such as lymphoma, leukemias, and immunodeficiency problems. The B-cells represent about 10-20% of the peripheral blood lymphocytes. The T-cells which are indicators of the cellular immune responses, i.e. delayed hypersensitivity and organ transplant rejection, constitute about 70-80% of the total. The lymphocyte subpopulations known as T-helper cells and T-suppressor cells, serve to regulate the antibody production and are effectors of T-cell functions. The enumeration of T-lymphocytes has diagnostic significance in certain chronic disorders where reduced numbers are found. Thus, monitoring the number of T-suppressor and T-helper cells has advanced the understanding and treatment of diseases affecting the immune system. The changes in the ratio of the T-helper or T-suppressor cells has been found to be important in allergy characterization. Monitoring relative changes in these numbers is an indication of a possible rejection in organ surgery transplant.

Chemotherapy patients have been monitored to maintain an immune competent state in guiding improvements in the prognosis of cancer patients. Chronic lymphocytic leukemia was often characterized by monoclonal proliferation of B-cells. More recently, T-helper variant, T-suppressor variant and Natural Killer cell variant have been observed, wherein leukemic lymphocytes share surface antigenic properties found in the corresponding normal lymphocyte subtype. Changes in the ratio of the T-helper cell to the T-suppressor cells have been frequently found in AIDS. The Natural Killer cells are postulated to constitute the body's first line of defense against carcinogenic influences. Presently, there is no established reproducable method for identifying the differences between the B-cells, T-suppressor cells, T-helper cells, and the Natural Killer cells with any known panoptic stain. Using dark field illumination the staining of parasitic cells, i.e. cells which contain and/or surrounded by parasites in the blood are also accurately delineated in accordance with this invention. Parasites from individuals known to be victims of parasitic attack such as in tropical fevers, i.e. maleria, can be identified by their specific color and patterns.

Over the past several decades it has become apparent that lymphocytes, once thought to be a single class of cells, are actually a heterogenous collection of multiple subpopulations. Early studies established that there were at least two major types of lymphocytes in the blood and in lymph nodes, namely T and B-cells. T-cells are believed to be involved in cell mediated immunity and constitute the largest number of lymphocytes in normal peripheral blood. B-cells are involved in humoral immunity and in the synthesis of antibodies and constitute a small portion of the total number of lmphocytes in normal blood.

Figure 3:
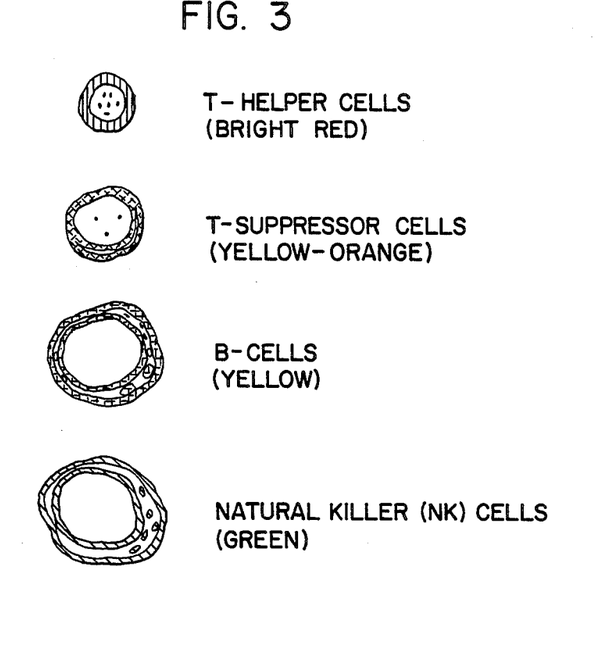
Figure 4:
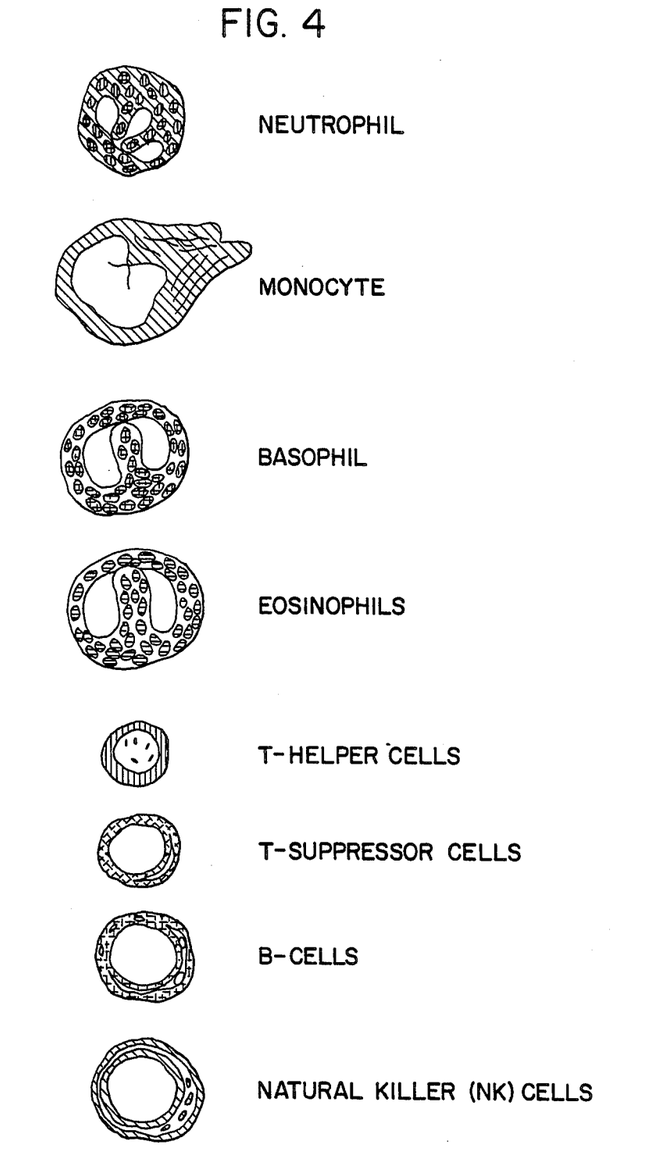

FIGS. 3 and 4 further illustrate the effectiveness of the three polymethine dyes, as defined herein, as a means of identifying and enumerating leukocyte subpopulations. FIG. 3 is an illustration of the leukocyte subpopulations, i.e. normal peripheral blood stained with Astrazon Red Violet FRR after FAA fixation (alcohol) and viewed under a dark field illuminations. FIG. 3 illustrates the shapes and colors of the T-helper cell, T-suppressor cell, B-cell (round or annular structure in cytoplasm), and the Natural Killer cell. In these lymphocytes, the nucleus and the cytoplasm are the structures that show the distinctive colors. In T-helper cells, the nucleus and the cytoplasm both stain bright red. In the T-suppressor cells, the cytoplasm stains yellow-orange together with the nucleus and membranes.

FIG. 4 shows normal peripheral blood cells stained with Astrazon Red Violet FRR after being fixed in FAA fixative (alcohol) and viewed under dark field illumination. The neutrophils were found to have faint green nuclear and cytoplasmic outlines with faint red to black granules. The monocytes showed a faint green nucleus and cytoplasmic outlines with a convoluted nucleus. The basophils showed bright yellow granules. The eosinophils showed bright sky blue granules. The T-helper cells showed red, the T-suppressor cells showed yellow-orange, the B-cells showed yellow and the Natural Killer cells showed green. For the most part, staining of the cytoplasm and membrane was more intense than staining of the nucleus.

There are generally two types of illumination, one where the images are formed by reflected light and another where images are being formed by scattered light so that the particles appear as bright light against a dark background. This can be accomplished by the use of dark field condenser producing a hollow cone of light focused on the plane of the specimen.

While this invention as been described by a number of specific examples, it is obvious that there are other variations which can be made without departing from the spirit and scope of the invention as particularly set forth in the appended claims.

The invention claimed is:

1. A method for differentiating, identifying and enumerating lymphocytes from one another among a plurality of cells of hematopoietic origin selected from the group consisting of blood cells, bone marrow cells and lymph node cells which comprises fixing a biopsy specimen of said cells in a fixative and subsequently staining said fixed cells with a staining amount of a polymethine dye to obtain a plurality of stained cells having individual color characteristics which permit the differentiation, identification and enumeration of the lymphocytes from one another and from a plurality of cells; said polymethine dye having the formula:

wherein R is a substituent selected from the group consisting of hydrogen, chlorine and CH$_3$—O—C═O.

2. The method of claim 1 further characterized in that the stained lymphocytes have color characteristics which permit the differentiation, identification and enumeration of said lymphocytes with an instrument under dark field illumination.

3. The method of claim 1 further characterized in that the polymethine dye has the formula wherein R is hydrogen.

4. The method of claim 1 further characterized in that the polymethine dye has the formula wherein R is CH$_3$—O—C═O.

5. The method of claim 1 further characterized in that the polymethine dye has the formula wherein R is chlorine.

6. The method of claim 1 further characterized in that the cells of hematopoietic origin are blood cells.

7. The method of claim 1 further characterized in that the cells of hematopoietic origin are cells having a subpopulation comprising T-helper cells, T-suppressor cells, B-cells, Natural Killer cells, eosinophils, basophils, neutrophils, monocytes, and platelets.

8. The method of claim 1 further characterized in that the fixative comprises a lower molecular weight alcohol.

9. The method of claim 1 further characterized in that the fixative comprises formaldehyde.

10. The method of claim 8 further characterized in that the fixative contains up to about 1.0 percent by weight of the polymethine dye.

11. The method of claim 1 further characterized in that the fixed cells are subsequently stained with the polymethine dye in an aqueous solution containing an alkaline buffering agent.

12. The method of claim 1 further characterized in that the cells are fixed in the fixative and then subsequently stained by the addition of staining amounts of an aqueous solution of the polymethine dye to the fixative.

13. The method of claim 12 further characterized in that an effective amount of an alkaline buffering agent is added to the aqueous solution of the polymethine dye to increase the pH.

14. The method of claim 13 further characterized in that the polymethine dye is present in the aqueous solution of the alkaline buffering agent in amounts ranging up to about 2.0 percent by weight of the solution.

15. The method of claim 1 further characterized in that the cells of hematopoietic origin are fixed in a solution containing ethyl alcohol and subsequently stained with an aqueous buffered solution of a polymethine dye having the formula wherein R is hydrogen.

16. The method of claim 1 further characterized in that the cells of hematopoietic origin are blood cells having a subpopulation comprising monocytes, platelets, eosinophils, basophils, neutrophils, T-suppressor cells, T-helper cells, B-cells, and Natural Killer cells.

17. The method of claim 16 further characterized in that the cells of hematopoietic origin comprise blood cells containing or surrounded by parasites.

18. The method of claim 16 further characterized in that the cells of hematopoietic origin comprise malignant cells.

19. The method of claim 1 further characterized in that the cells of hematopoietic origin comprise malignant blood cells.

20. The method of claim 16 further characterized in that the color characteristics of the stained cells permit the differentiation, identification and enumeration of said cells with an instrument under dark field illumination.

21. A plurality of cells of hematopoietic origin selected from the group consisting of blood cells, bone marrow cells, and lymph node cells fixed and stained with a polymethine dye; said stained cells having color characteristics which permit the differentiation, identification and enumeration of each stained cell among a plurality of the cells; said polymethine dye having the formula:

wherein R is a substituent selected from the group consisting of hydrogen, chlorine and $CH_3-O-C=O$.

22. The plurality of stained cells of claim 21 further characterized in that the polymethine dye has the formula wherein R is hydrogen.

23. The plurality of stained cells of claim 21 further characterized in that the polymethine dye has the formula wherein R is $CH_3-O-C=O$.

24. The plurality of stained cells of claim 21 further characterized in that the polymethine dye has the formula wherein R is chlorine.

25. The plurality of stained cells of claim 22 further characterized as stained blood cells having a subpopulation comprising T-helper cells, T-suppressor cells, B-cells, Natural Killer cells, neutrophils, basophils, eosinophils, monocytes, and platelets.

26. The plurality of stained cells of claim 22 further characterized as stained lymphocyte subpopulation.

27. The plurality of stained cells of claim 26 further characterized in that the stained lymphocyte subpopulation comprise malignant cells.

28. The plurality of stained cells of claim 21 further characterized as stained human blood cells of hematopoietic origin comprising lymphocyte subpopulation containing or surrounded by parasites.

29. The plurality of stained cells of claim 28 further characterized in that the lymphocyte subpopulation are stained with the polymethine dye having the formula wherein R is hydrogen.

30. The plurality of stained cells of claim 21 further characterized in that the color characteristics of the stained cells permit the differentiation, identification and enumeration of the stained lymphocyte with an instrument under dark field illumination.

* * * * *